(12) United States Patent
Hoessel et al.

(10) Patent No.: US 11,382,854 B2
(45) Date of Patent: Jul. 12, 2022

(54) POLYMER

(71) Applicants: BASF SE, Ludwigshafen (DE); BASF ESPANOLA S.L., Barcelona (ES); BASF Interservicios S.A. de C.V., Mexico City (MX); BASF PLC, Cheadle (GB)

(72) Inventors: Peter Hoessel, Ludwigshafen (DE); Christian Schade, Ludwigshafen (DE); Cristina Amela, Barcelona (ES); Bianca Seelig, Monheim (DE); Andrea Tomlinson, Cheadle (GB); Volker Wendel, Düsseldorf-Holthausen (DE); Rolf Werner, Ludwigshafen (DE); Luis Angel Ibarra, Ecatepec de Morelos (MX)

(73) Assignees: BASF SE, Ludwigshafen (DE); BASF Interservicios S.A. de C.V., Mexico City (MX); BASF ESPANOLA S.L., Barcelona (ES); BASF PLC, Cheadle (GB)

( * ) Notice: Subject to any disclaimer, the term of this patent is extended or adjusted under 35 U.S.C. 154(b) by 0 days.

(21) Appl. No.: 16/481,521

(22) PCT Filed: Jan. 31, 2018

(86) PCT No.: PCT/EP2018/052409
§ 371 (c)(1),
(2) Date: Jul. 29, 2019

(87) PCT Pub. No.: WO2018/145973
PCT Pub. Date: Aug. 16, 2018

(65) Prior Publication Data
US 2019/0388331 A1 Dec. 26, 2019

(30) Foreign Application Priority Data
Feb. 7, 2017 (EP) .................................. 17155003

(51) Int. Cl.
*A61K 8/81* (2006.01)
*A61Q 5/06* (2006.01)
*C08F 220/12* (2006.01)

(52) U.S. Cl.
CPC .............. *A61K 8/8152* (2013.01); *A61Q 5/06* (2013.01); *C08F 220/12* (2013.01); *A61K 2800/48* (2013.01)

(58) Field of Classification Search
None
See application file for complete search history.

(56) References Cited

U.S. PATENT DOCUMENTS 4,269,749 A 5/1981 Marriott et al.

FOREIGN PATENT DOCUMENTS

| EP | 0184785 A2 | 6/1986 | |
|---|---|---|---|
| EP | 0184785 B1 * | 9/1991 | ............... A61Q 5/08 |
| GB | 870994 A | 6/1961 | |
| GB | 2053937 A | 2/1981 | |
| WO | WO-2011/135039 A1 | 11/2011 | |
| WO | WO-2012/031113 A2 | 3/2012 | |
| WO | WO-2014099512 A2 * | 6/2014 | ........... A61K 8/8182 |

OTHER PUBLICATIONS

International Application No. PCT/EP2018/052409, International Search Report and Written Opinion, dated Mar. 28, 2018.

* cited by examiner

*Primary Examiner* — Bong-Sook Baek
(74) *Attorney, Agent, or Firm* — Marshall, Gerstein & Borun LLP

(57) ABSTRACT

A polymer having the following monomers in polymerized form (in weight %): A) 49-60% of a first monomer which is selected from the group consisting of methyl acrylate, methyl methacrylate, ethyl acrylate, ethyl methacrylate, C3-alkyl acrylate, C3-alkyl methacrylate, C4-alkyl acrylate, C4-alkyl methacrylate and mixtures thereof, B) 30-40% methacrylic acid, C) 4-15% acrylic acid, and D) 0.02-0.30% of a crosslinking agent having at least two allyl moieties, wherein the sum of the amounts of monomers A to D is 100%. A hair styling composition containing the polymer and use of the polymer or of the hair styling composition for styling hair also are disclosed.

15 Claims, No Drawings

POLYMER

CROSS REFERENCE TO RELATED APPLICATIONS

This application is the U.S. National Stage application of International Patent Application No. PCT/EP2018/052409, filed Jan. 31, 2018, which claims the benefit of European Patent Application No. 17155003.1, filed Feb. 7, 2017.

The present invention relates to a polymer comprising the following monomers in polymerized form (in weight %): A) 49-60% of a first monomer which is selected from the group consisting of methyl acrylate, methyl methacrylate, ethyl acrylate, ethyl methacrylate, C3-alkyl acrylate, C3-alkyl methacrylate, C4-alkyl acrylate, C4-alkyl methacrylate and mixtures thereof, B) 30-40% methacrylic acid, C) 4-15% acrylic acid, and D) 0.02-0.30% of a crosslinking agent which is a compound having at least two allyl moieties, wherein the sum of the amounts of monomers A to D is 100%. Furthermore, the present invention relates to a hair styling composition comprising the polymer and to the use of the polymer or of the hair styling composition for styling hair.

Conventional hair styling gels are based on polyvinylpyrrolidone (PVP) and/or copolymers of vinyl pyrrolidone and vinyl acetate (VP/VA copolymers) and carbomer (cross-linked polyacrylic acid) for thickening/rheological properties. Drawback of those formulations is low curl retention and less styling performance at low styling polymer contents between 1 and 2% by weight solids. In some markets, especially in emerging markets, a low solids content is important to keep costs of formulations as low as possible without sacrificing styling performance.

Alternatives to PVP and VP/VA copolymers are acrylate based styling polymers. Acrylate based styling polymers have improved styling performance compared to PVP and VP/VA copolymers. However, the compatibility of known and commercially available polyacrylates with carbomer is limited because the styling polymer reduces the thickening power of carbomer in a way that it is impossible to achieve styling gels with "no flow" behavior. Examples for those polyacrylates that do not provide no flow behavior in simple formulations (1.0-5.0% by weight solids content) in combination with carbomer thickeners (0.1-1.0% by weight solids content) are acrylates copolymer (Luviflex® Soft), AMP-acrylates/allyl methacrylate copolymer (Carbopol® Fixate G-100), Polyacrylate-14 (Carbopol® Fixate Plus), acrylates crosspolymer-3 (Carbopol® Fixate Free Style), polyacrylate-2 crosspolymer (Carbopol® Fixate Superhold) and acrylates/methacrylamide copolymer (Luviset® One).

WO 2011/135039 (BASF-internal file no. PF 70726) discloses a copolymer and its use for hair styling and for increasing the viscosity of cosmetic compositions. The copolymer, according to claim 1 of this document must comprise at least four different monomers and can optionally comprise further monomers. Example 21 on page 42 of this document discloses the following composition (in % by weight): EA (ethyl acrylate): 46.7%, MAS (methacrylic acid): 41.6%, PETAE (pentaerythritol triallyl ether): 0.1%, MAM (methacryl amide): 10% and Lutencryl (an ethoxylated fatty alcohol) methacrylate): 1.6%. According to the teaching of WO 2011/135039 as outlined on page 1, line 11 to page 2, line 9 a polymer that has good styling properties and good thickening (viscosity improving) properties must comprise an associative polymer and nitrogen-born hydrogen.

The problem underlying the present invention is to provide a polymer that has good hair styling properties. It is advantageous if this polymer can form transparent aqueous gel at a pH value of 7. It is furthermore advantageous if this polymer increases the viscosity of aqueous solutions, i. e. has a good thickening effect.

This problem is solved by the polymer according to claim 1. The dependent claims are directed to preferred embodiments of the polymer according to the present invention. Further claims are directed to further subjects of the present invention, namely a hair styling composition comprising the polymer according to the present invention and the use of the polymer according to the present invention or of the hair styling composition according to the present invention for styling hair.

As has been said before the dependent claims are directed to preferred embodiments of the polymer according to the present invention. Amongst these preferred embodiments those embodiments are preferred in which the first monomer is ethyl acrylate and the crosslinking agent is pentaerythritol triallylether (PETAE).

Some of the polymers according to the present invention, in addition to good styling performance, provide "no flow" of a styling gel comprising this polymer at a concentration of 0.5 to 3.0% by weight polymer in combination with carbomer-type thickeners (crosslinked polyacrylic acid) in cosmetically suitable containers.

"No flow" behavior means a very high viscosity of a styling formulation, so that it is possible to have the styling formulation in a vessel common for cosmetic products, to turn the vessel slowly upside down, and still the formulation does not flow out of the vessel within minutes.

Good styling performance comprises high bending stiffness and high curl retention and low flaking.

Furthermore, it is advantageous if those styling gel formulations can be made transparent with the polymers according to the present invention.

Some of the polymers according to the present invention, in addition to providing good styling performance, can be used to make "no flow" transparent styling formulations at a polymer concentration in the formulation of higher that 3% by weight, e.g. 4% by weight without having additional thickener, e. g. crosslinked polycarboxylic acid, in the formulation.

Pentaerythritol triallyl ether may comprise the neat compound or mixtures of pentaerythritol, pentaerythritol mono-, di- tri- and tetra-allylether with an average composition of allyl ether/pentaerythritol of 2.2 to 3.8.

Thickeners that may be used in the compositions according to the present invention can be, inter alia, crosslinked polyacrylic acid (INCI: Carbomer®), available in the market e. g. as Carbopol® 940, 980 and others.

Other thickeners that may be uses are Carbopol® Ultrez-grades, e.g. Ultrez® 10, 20, 21, Salcare®-grades, e.g. Salcare® SC80 and 81, Aculyn®-grades from Röhm, e.g. Aculyn® 33, 22, 28, 88, Synthalen®—grades from Sigma 3V, e.g. Synthalen® 3001, W 2000, Tinovis® GTC, Luvigel® FIT (UP), Rheocare® C Plus, Rheocare® 400, Rheocare® TTA.

Other thickeners that may be uses are different types of polyacrylic acids and cross-linked polyacrylic acids (e.g. INCI: Carbomer), associative thickeners with hydrophobic monomers in addition to methyacrylic acid and ethyl acylate, not cross-linked or in addition cross-linked (e.g. INCI: Steareth-10 Allyl Ether/Acrylates Copolymer, Acrylates Copolymer(s), Acrylates/Steareth-20 Methacrylate Copolymer, Acrylates/Beheneth-25 Methacrylate Copolymer, Acrylates/Palmeth-25 Acrylate Copolymer, Acrylates/C10-C30 Alkyl Methacrylate Copolymer), polyacrylic acids with hydrophobic monomers, crosslinked; (e.g. INCI: Acrylates/C10-30 Alkyl Acrylates Crosspolymer(s)).

The following paragraphs describe methods that can be used for making the polymer according to the present invention.

The monomers can be polymerized preferably by free-radical means or, where possible, anionically. As customary polymerization methods, both free-radical and anionic polymerization are familiar to the person skilled in the art.

Free-radical polymerization can be carried out, for example, in solution, such as in an organic solvent (solution polymerization), in aqueous dispersion (emulsion polymerization, suspension polymerization) or in bulk, i.e. essentially in the absence of water or organic solvents (bulk polymerization).

The emulsion polymerization can be carried out using ionic and/or nonionic emulsifiers and/or protective colloids and/or stabilizers as surface-active compounds. The general technique of emulsion polymerisation is known to the person skilled in the art.

Examples of suitable protective colloids are polyvinyl alcohols, starch derivatives and cellulose derivatives, or vinyl pyrrolidone copolymers. Mixtures of emulsifiers and/or protective colloids may also be used. It is preferred to use as surface-active compounds exclusively emulsifiers, whose relative molecular weights are usually below 2000 g/mol. Preference is given to the use of at least one anionic emulsifier, alone or in combination with a nonionic emulsifier.

Anionic emulsifiers include alkali metal salts or ammonium salts of alkyl sulfates (alkyl: $C_8$-$C_{22}$), of dialkyl esters of sulfosuccinic acid (alkyl: $C_4$-$C_{10}$), of sulfuric monoesters with ethoxylated alkanols (EO units: 2 to 50, alkyl: $C_8$ to $C_{22}$) and with ethoxylated alkylphenols (EO units: 3 to 50, alkyl: $C_4$-$C_{10}$), of alkylsulfonic acids (alkyl: $C_{12}$-$C_{18}$) and of alkylarylsulfonic acids (alkyl: $C_9$ to $C_{18}$). The anionic surface-active compounds also include monoalkyl and dialkyl derivatives of sulfonylphenoxybenzenesulfonic acid salts, especially their sodium, potassium or calcium salts. The alkyl groups in these compounds have generally 6 to 18 and especially 6, 12 or 16 carbon atoms. Use is frequently made of technical mixtures containing a fraction of from 50 to 90 wt % of the monoalkylated product. These compounds are general knowledge, from U.S. Pat. No. 4,269,749, for example, and are obtainable commercially, for example, as Dowfax® 2A1 (trademark of the Dow Chemical Company).

Suitable nonionic emulsifiers are araliphatic or aliphatic nonionic emulsifiers, examples being ethoxylated mono-, di- and trialkylphenols (EO units: 3 to 50, alkyl: $C_4$-$C_9$), ethoxylates of long-chain alcohols (EO units: 3 to 50, alkyl: $C_8$-$C_{36}$), and also polyethylene oxide/polypropylene oxide block copolymers. Further nonionic emulsifiers include alcoxylated ($C_2$-$C_{16}$ alcoxide; alone, in mixture or sequentially added) saturated or unsaturated, linear, branched or cyclic alcohols (EO units: EO units: 3 to 50; monoalcohols and compounds with more than one hydroxy function), optionally esterified or etherified with $C_8$ to $C_{22}$ araliphatic or aliphatic compounds. Preference is given to ethoxylates of long-chain alkanols (alkyl: $C_{10}$-$C_{22}$, average degree of ethoxylation: from 3 to 50) and, of these, particular preference to those based on oxo alcohols and naturally occurring alcohols having a linear or branched $C_{12}$-$C_{20}$ alkyl radical and a degree of ethoxylation of from 8 to 50. Further particularly preferred nonionic emulsifiers include a polysorbate, and preferably polysorbate 20 or polysorbate 80 (commercially available as Crillet® 4).

The surface-active compounds preferably include alkali metal salts of $C_8$-$C_{12}$ alkyl sulfates or alkoxylated alkyl sulfates (EO units: 2 to 50, alkyl: $C_{12}$ to $C_{22}$), more preferably sodium lauryl sulfate, sodium lauryl ether sulfate, or polysorbate, and preferably polysorbate 20 or polysorbate 80 (commercially available as Crillet® 4), or mixtures thereof.

The surface-active compound is normally used in an amount of preferably 0.1 to 10 wt %, more preferably 0.5 to 5 wt %, based on weight of the monomers that are to be polymerized. It is also possible to use a plurality of different surface-active compounds in the course of emulsion polymerization.

Examples of water-soluble initiators which can be used for emulsion polymerization are ammonium salts and alkali metal salts of persulfuric acid, e.g. sodium persulfate, hydrogen peroxide or organic peroxides, e.g. tert-butyl hydroperoxide.

Reduction-oxidation (redox) initiator systems are particularly suitable, consisting of at least one, usually inorganic reducing agent and of an inorganic or organic oxidizing agent.

The oxidation component comprises, for example, the above-mentioned initiators for emulsion polymerization.

The reduction component comprises, for example, alkali metal salts of sulfurous acid, such as sodium sulfite, sodium hydrogen sulfite, alkali metal salts of disulfurous acid, such as sodium disulfite, bisulfite addition compounds with aliphatic aldehydes and ketones, such as acetone bisulfite, or reducing agents such as hydroxymethanesulfinic acid and its salts, or ascorbic acid. The redox initiator systems can be used along with soluble metal compounds whose metallic component is able to exist in a plurality of valency states.

Examples of common redox initiator systems are ascorbic acid/iron (II) sulfate/sodium peroxodisulfate, tert-butyl hydroperoxide/sodium disulfite, and tert-butyl hydroperoxide/Na hydroxymethanesulfinate. The individual components, for example the reduction component, may also be mixtures, for example a mixture of the sodium salt of hydroxymethanesulfinic acid with sodium disulfite.

The above mentioned initiators are mostly employed in the form of aqueous solutions, the lower concentration being determined by the amount of water which is acceptable in the dispersion and the upper concentration by the solubility of the relevant compound in water. In general the concentration is from 0.1 to 30 wt %, preferably from 0.5 to 20 wt %, particularly preferably from 1.0 to 10 wt %, based on the solution.

The amount of initiators is generally from 0.01 to 10 wt %, preferably from 0.05 to 5 wt %, more preferably from 0.1 to 2 wt %, based on weight of the monomers that are to be polymerized. It is also possible to use a plurality of different initiators in the course of emulsion polymerization.

The polymerization may be run in a manner known in the art. Preferred reaction temperatures are in the range 30-130° C., preferably 60-95° C., with a final solids content of 20-50 w.-%, preferably 25-35%. Monomers and initiators may be charged batch or fed during the reaction time; typical monomer feed times encompass 1 to 4 hours.

Needless to say, the compositions of the present invention should be cosmetically or dermatologically acceptable, i.e., it should contain a non-toxic physiologically acceptable medium and should be able to be applied to the hair of human beings. For the purposes of the invention, the expression "cosmetically acceptable" means a composition of pleasant appearance, odor, feel and/or taste.

The hair styling polymers according to the present invention can be used for improving the rheology by means of no/low flow behavior or the final hair styling gel in combination with good appearance of the gel, e.g. transparent gels and gels that have a smooth texture and excellent hair styling performance, e.g. high setting performance, humidity resistance and low flaking (visible particles on hair after combing).

Further substances that may be used as components of the hair styling composition according to the present invention are (preferred amount in % by weight): glycerol (0-20%), sorbitol (0-20%), propylene glycol (0-20%), silicones, silicone copolyols (0-5%), ethanol (0.30%), propane/butane (5-15%), HFC152a (1,1-difluoro ethane) (5-15%), blend of propane/butane and HFC 152a (5-15%), 1,3,3,3-tetraflouro propene (5-15%), fragrances, solubilizer, emulsifiers, preservatives; sodium benzoate preferred (0.3-1.0%), panthenol (0-5%), neutralization agents (aminomethyl propanol, triethanol amine, KOH, NaOH, others), additional styling polymers, e.g. PVP polymers and copolymers (0-3%), anionic polymers (0-3%), cationic polymers (0-1%), pigments, colors, UV-filters, semi-permanent hair dyes (cationic, anionic).

The polymer according to the present invention can also be used as a component of sun care emulsions.

The composition according the present invention can comprise a cosmetically acceptable carrier, e. e. a cosmetically acceptable carrier as defined in WO 2011/135039, page 25, last paragraph to page 26, first paragraph. It can furthermore comprise additives as defined in WO 2011/135039, page 26, second and third paragraph.

EXAMPLES

Polymer Synthesis
Materials

Pentaerythritol triallylether used consisted of approximately 70% pentaerythritol triallyl-ether, the remainder being the corresponding di- and tetraallylether.

Example 1 (Polymer 1)

In a polymerization reactor a mixture of 440 g water and 1.4 g sodium laurylsulfate were heated under stirring to 75° C. At that temperature a stirred emulsion of 340 g water, 1 g sodium lauryl sulfate, 9 g polysorbate 80, 190 g ethyl acrylate, 160 g methacrylic acid and 0.4 g pentaerythritol triallyether (PETAE) was fed over 2.5 hours and parallel a feed of 1 g sodium peroxidisulfate over 3 hours.

A white dispersion with a solid content of 30 w.-% and a pH-value of 2.6 was obtained. A 4 w.-% aqueous gel of this product with pH value of 7 was transparent and had a Brookfield viscosity (spindle 6, 20 rpm) of 21 Pas.

In a similar manner examples 2 to 3 have been synthesized; composition see Table 1:

TABLE 1

| | Composition of Polymers (w.-%) | | | |
|---|---|---|---|---|
| Polymer | Ethyl acrylate (EA) | Methacrylic acid (MAS) | Acrylic acid | PETAE |
| 1 | 54.33 | 45.46 | 0 | 0.21 |
| 2 | 54.33 | 40.91 | 4.55 | 0.21 |
| 3 | 54.33 | 36.36 | 9.10 | 0.21 |

Comparative Example (Variation of Acrylic Acid) (Polymer 4)

Example 3 was repeated with a monomer ratio of ethyl acrylate:methacrylic acid:acrylic acid of 54.4:28.5:17. In the course of the reaction massive coagulum formation appeared.

Comparative Example (Variation of Crosslinker Amount) (Polymers 5 and 6)

| | Monomer Ratio in % | | | |
|---|---|---|---|---|
| Polymer | EA | MAS | PETAE | Remarks |
| 5 | 54 | 46 | 0.43 | waxy, turbid material |
| 6 | 54 | 46 | 0.36 | turbid gel |

Increase in PETAE leads to viscous, yet turbid gels (2 w.-% polymer in water, pH=7, base: NaOH)

Comparative Example (Variation of Crosslinker Type) (Polymers 7 to 15)

Acrylate1 is a triacrylate ester of glycerol ethoxylate with on average 3 ethyleneoxide units. EGDMA is ethyleneglycol-bis(methacrylate), MBA is methylene-bis(acrylamide)

| | Monomer Ratio in % | | | | Gel viscosity | |
|---|---|---|---|---|---|---|
| Polymer | EA | MAS | Crosslinker | % | 2% | 4% |
| 7 | 54 | 46 | Diallylphthalate | 0.14 | | 22400 clear |
| 8 | 54 | 46 | Diallylphthalate | 0.20 | | 25600 clear |
| 9 | 54 | 46 | EGDMA | 0.11 | | 4450 |
| 10 | 54 | 46 | EGDMA | 0.22 | | 5100 |
| 11 | 54 | 46 | Acrylate1 | 0.15 | 6250 | 17850 |
| 12 | 54 | 46 | Acrylate1 | 0.30 | 4400 | 11550 |
| 13 | 54 | 46 | MBA | 0.09 | | 14650 turbid |
| 14 | 54 | 46 | MBA | 0.18 | | 15500 turbid |
| 15 | 54 | 46 | MBA | 0.30 | | 21100 turbid |

"Gel viscosity" was obtained by adding the polymer in the amount shown to water and adjusting the pH to a value of 7 by adding aminomethylpropanole. Gel viscosities were measured in mPas at 21° C. (Brookfield RVT, sp. 7, 20 rpm). The examples show that non-allylic crosslinkers (e. g. (meth)acrylic ester and acryl amide derivatives) lead to a reduced thickening effect of aqueous systems and/or turbid gels.

Chassis Formulations

The formulations vide infra are basic formulations to compare the inventive polymer with conventional polymers. These are already practically relevant and are used in market styling gels, however some market gels contain different additives, e.g. glycerol, propylene glycol, emulsifiers and solubilizers, silicones, UV-filters, EDTA and other complexing agents, perfumes, ethanol, isopropanol, different emollients and preservatives.

TABLE 2

Basic formulation No. 1 with 1.0% (weight percent polymer No. 3)

| Amount [wt %] | Ingredient | INCI | Supplier |
|---|---|---|---|
| 1.00 | Polymer 3 (this invention) | Acrylates Copolymer (applied for) | BASF |
| 0.95 | AMP Ultra PC2000 | Aminomethyl-propanol | Angus |
| 0.80 | Carbopol ® 980 | Carbomer | Lubrizol |
| 0.50 | Euxyl ® PE 9010 | Phenoxyethanol, Ethylhexylglycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 3

Basic formulation No. 2 with 2.0% (weight percent polymer No. 3)

| Amount [wt %] | Ingredient | INCI | Supplier |
|---|---|---|---|
| 2.00 | Polymer 3 (this invention) | Acrylates Copolymer (applied for) | BASF |
| 1.33 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexylglycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 4

Basic formulation No. 3 with 4.0% (weight percent polymer No. 3)

| Amount [wt %] | Ingredient | INCI | Supplier |
|---|---|---|---|
| 4.00 | Polymer 3 (this invention) | Acrylates Copolymer (applied for) | BASF |
| 1.60 | AMP Ultra PC2000 | Aminomethyl-propanol | Angus |
| 0.00 | Carbopol ® 980 | Carbomer | Lubrizol |
| 0.50 | Euxyl ® PE 9010 | Phenoxyethanol, Ethylhexylglycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 5

Basic formulation No. 4 with 2.0% (weight percent polymer No. 2)

| Amount [wt %] | Ingredient | INCI | Supplier |
|---|---|---|---|
| 2.00 | Polymer 2 (this invention) | Acrylates Copolymer (applied for) | BASF |
| 1.33 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexylglycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 6

Basic formulation No. 5 with 2.0% (weight percent polymer No. 1)

| Amount [wt %] | Ingredient | INCI | Supplier |
|---|---|---|---|
| 2.00 | Polymer 1 (this invention) | Acrylates Copolymer (applied for) | BASF |
| 1.33 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexylglycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 7

Comparison formulation No. 6 with 2.0% Luviskol ® K90 (weight percent polymer)

| Amount [wt %] | Ingredient | INCI | Supplier |
|---|---|---|---|
| 2.00 | Luviskol K90 | PVP | BASF |
| 0.50 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexylglycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 8

Comparison formulation No. 7 with 2.0% Luviskol ® VA 64 (weight percent polymer)

| Amount [wt %] | Ingredient | INCI | Supplier |
|---|---|---|---|
| 2.00 | Luviskol ® VA 64 | VP/VA Copolymer | BASF |
| 0.50 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexylglycerin | Schülke&Mayr |

TABLE 8-continued

Comparison formulation No. 7 with 2.0% Luviskol ® VA 64 (weight percent polymer)

| Amount [wt %] | Ingredient | INCI | Supplier |
|---|---|---|---|
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 9

Comparison formulation No. 8 with 2.0% Luviskol ® K30 (weight percent polymer)

| Amount [wt %] | Ingredient | INCI | Supplier |
|---|---|---|---|
| 2.00 | Luviskol ® K 30 | PVP | BASF |
| 0.50 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexyl-glycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

TABLE 10

Comparison formulation No. 9 with 2.0% Carbopol ® Fixate Freestyle (weight percent polymer)

| Amount [wt %] | Ingredient | INCI | Supplier |
|---|---|---|---|
| 2.00 | Carbopol ® Fixate Freestyle | Acrylates Crosspolymer-3 | Lubrizol |
| 1.20 | AMP Ultra PC2000 | Aminomethyl-propanol | Angus |
| 0.50 | Carbopol ® 980 | Carbomer | Lubrizol |
| 0.50 | Euxyl ® PE 9010 | Phenoxyethanol, Ethylhexyl-glycerin | Schülke&Mayr |
| 0.30 | Cremophor ® CO40 | PEG-40 Hydrogenated Castor Oil | BASF |
| Add 100 | Water | Aqua | |

Adapt to pH 6.9-7.0 with AMP Ultra PC2000

Test Methods

1. Gel Transparency

The transmission in a 1 cm cuvette (%) was recorded by means of a UV-Visible Spectrophotometer at 600 nm, Cary 300 Scan, Agilent Technologies and by means of subjective optical assessment (clear, slightly turbid, turbid).

2. Gel Flow

A 100 ml glass container filled with 75 ml styling gel was turned on side (90 degree). Time was measured in hours to allow the gel to flow for a distance of 2 cm.

3. Viscosity Brookfield

Gels viscosities were measured in mPas at 21° C. with (Brookfield RVT, sp. 7, 20 rpm).

4. Viscosity (mPas) at 0.1 T (Shear Stress)

Rheology was measured by means of a Haake RS-1-Rheometer by 20° C. in Plate/Plate system. The measurement was performed by shear stress mode (CS-mode, controlled-stress-mode) in a range of 0.001 Pa until 1000 Pa. The rheometer worked with a PP 35 Ti plate (diameter 35 mm). Measuring gap 1 mm and measuring time 180 s. The viscosity at low shear stress was in good correlation with the no flow properties of the hair styling gels in containers.

5. Bending Stiffness (in cN)

The final gel formulations (formula 1 to 7) were diluted with water (6 g gel and 24 g water). The flat hair strands (Caucasian hair, dark brown from IHIP—International Hair Importers, 1.8 g tied hair, 2 cm width and 8 cm length) were applied with 1.4 g diluted gel per strand. Each formulation was tested on 7 hair strands.

1.4 g of the diluted gel was applied and distributed in one direction from root to tip by means of a dyeing brush. After turning the hair strand to 180° the same procedure was repeated. The treated hair strands were unclamped and combed with the fine side until the strand was homogeneous. The scattered parts were brought together between 2 fingers without exerting pressure. The treated hair strands were put in a mould of polyethylene (PE). A metal cylinder was rolled over the strand without exerting pressure. Then the strands were aligned vertically in a rack in a climate chamber at 65% humidity and 21° C. for drying overnight. The maximum bending force (in cN) of the hair/polymer composite was measured in a tensile tester (Type: Texture Analyzer-TA.XTPlus).

6. Curl Retention in %

The hair gels were diluted with water in a ratio 1:2 with. 1.5 g of the diluted gel was spread over the hair strain (tied round-shaped hair strands, 2.0 g, 15.0 cm, IHIP International Hair Importers) and spread in one direction from root to tip by means of a dyeing brush. The prepared hair strands (5 each) were put on a hair curler and were dried overnight at 40° C. The curls were removed from the curler and were hung up at one end and their starting length was recorded. The determination of the curl retention was performed at 25° C. and 90% relative humidity in a climate chamber. After 5 hours, the final length of the curls was recorded. The stability of the curls in the particular climate was calculated and given in percent.

The Curl Retention was calculated by the following equation:

$$\text{Curl retention in \%} = (L - Lt/L - Lo) + 100$$

L=length of hair (15 cm)
Lo=length of hair Curl (start)
Lt=length of hair curl after period of time 7. Flaking Flaking was assessed by trained hairdressers on European mid brown hair strands (sewn hair strands, 12.5-13.5 g, 23×6 cm, Haarkunst GmbH Wernesgruen). The application (1.0 g gel on each side of the hair tress) was done in a climate controlled room at 20° C., 65% relative humidity. Testing was performed after 3 hours drying time. The flaking rating was an assessment of visible residues on the hair tresses after combing with the coarse-toothed part of a comb based on a blend of natural rubber and hard rubber. The visible flaking was rated on a scale of 1-4:1 (no flaking), 2 (low flaking), 3 (obvious flaking) and 4 (very much flaking; not acceptable). The graduations "+" and "−" indicate slightly better or slightly worse.

8. Running on Hand

The gel flow on the hand of a consumer was simulated by a ramp. A pane of glass was used as a ramp (65°) in a closed glass container. The glass plate was covered with a filter paper drained with water and an artificial sweatener[1] (0.3 g of the gel was applied on the filter paper with a syringe).

Then, the time (in seconds) that the gel needs to flow 5 cm down the ramp was detected.

1) Synthetic Sweat: ISO 3160/2 comprising of 20 g/l NaCl, 17.5 g/l NH4Cl, 5 g/l Acetic Acid and 15 g/l Lactic Acid; pH adjusted to 4.7 by NaOH Test Results

TABLE 11

Test results with inventive polymer in chassis styling gel formulations in comparison to conventional styling polymers

| | | | | Method No. | | | | |
|---|---|---|---|---|---|---|---|---|
| Polymer | Gel formulation No. | 1 % | 2 hours | 3 mPas (Brook field) | 4 mPas (at 0.1 tau shear stress) | 5 centi Newton (cN) | 6 % | 7 rating (from 1-4) | 8 min |
| Nr. 3 | 1 | 91 | 4 | 47000 | 28000 | 218 ± 19 | 62 ± 9 | 1 | 5 |
| Nr. 3 | 2 | 88 | 4 | 35000 | 12000 | 315 ± 26 | 79 ± 3 | 2 | 6 |
| Nr. 3 | 3 | 100 | 24 | 35000 | 18000 | 598 ± 57 | 100 | 2 | 10 |
| Nr. 2 | 4 | 79 | 3 | 26400 | 12000 | 332 ± 35 | 76 ± 3 | 2 | 6 |
| Nr. 1 | 5 | 67 | 3 | 37000 | 12000 | 349 ± 31 | 75 ± 2 | 2 | 6 |
| Luviskol ® K90 | 6 | 88 | 24 | 68000 | 15000 | 261 ± 19 | 30 ± 4 | 3 | 0 |
| Luviskol ® VA64 | 7 | 92 | 3 | 41000 | 20000 | 161 ± 16 | 33 ± 4 | 2-3 | 0 |
| Luviskol ® K30 | 8 | 89 | 3 | 39000 | 18000 | 152 ± 15 | 30 ± 3 | 2-3 | 4 |
| Carbopol ® Fixate FreeStyle | 9 | 78 | 0 | 11600 | 2500 | 287 ± 25 | 84 ± 4 | 3 | 0 |

Luviskol® is a polyvinyl pyrrolidone polymer.

Carbopol® Fixate FreeStyle has the INCI name acrylates crosspolymer-3.

Inventive polymer No 3 (see table 1) in this invention provides the best combination of rheology performance and styling performance in styling gel formulations at a polymer concentration between 1 to 4% by weight polymer content.

The direct comparison (formulation no. 2 with polymer no. 3 in table 3) with conventional polymers at same solids content is given in table 11.

The inventive polymer 3 in the formulas 1-3 provides much better bending stiffness (method 5), curl retention (method 6) and less flaking (method 7) than formulations with PVP polymers (formulations 6-8) without sacrificing low flow (method 2) of the styling gel.

The inventive polymer 3 in the formulas 1-3, specifically at same solids content in formula 2 provides more transparency (1), no flow behavior (2) and better salt tolerance (8) than Carbopol® FixateFreeStyle in formula 9.

The inventive polymer 3 (formula 2) with the largest amount of acrylic acid provides better gel clarity (1) and no flow behavior (2) compared to the inventive polymers 1 and 2 with no respectively less acrylic acid in the formulas 4 and 5.

The invention claimed is:

1. A polymer comprising the following monomers in polymerized form (in weight %):
    A) 49-60% of a first monomer which is selected from the group consisting of methyl acrylate, methyl methacrylate, ethyl acrylate, ethyl methacrylate, C3-alkyl acrylate, C3-alkyl methacrylate, C4-alkyl acrylate, C4-alkyl methacrylate, and mixtures thereof,
    B) 30-40% methacrylic acid,
    C) 4-15% acrylic acid, and
    D) 0.02-0.30% of a crosslinking agent which is a compound having at least two allyl moieties,
    wherein the sum of the amounts of monomers A to D is 100%.

2. The polymer according to claim 1 comprising the following monomers in polymerized form (in weight %):
    A) 50-60% of the first monomer,
    B) 30-40% methacrylic acid,
    C) 4-15% acrylic acid, and
    D) 0.05-0.25% of the crosslinking agent,
    wherein the sum of the amounts of monomers A to D is 100%.

3. The polymer according to claim 1 comprising the following monomers in polymerized form (in weight %):
    A) 50-60% of the first monomer,
    B) 30-40% methacrylic acid,
    C) 4-10% acrylic acid, and
    D) 0.10-0.25% of the crosslinking agent,
    wherein the sum of the amounts of monomers A to D is 100%.

4. The polymer according to claim 1 comprising the following monomers in polymerized form (in weight %):
    A) 53-56% of the first monomer,
    B) 35-38% methacrylic acid,
    C) 7-11% acrylic acid, and
    D) 0.05-0.30% of the crosslinking agent,
    wherein the sum of the amounts of monomers A to D is 100%.

5. The polymer according to claim 1, wherein the crosslinking agent is selected from the group consisting of pentaerythritol triallylether, a sucrose allyl ether having at least two allyl groups, a sorbitol allyl ether having at least two allyl groups, diallylphthalate, 1,3,5-triallyl-1,3,5-triazin-2,4,6-(1H,3H,6H)-trione, triallylamine, tetraallylammonium chloride, diallylamine, N,N'-diallylurea, a diallylated pentaerythritol-ether-condensate, triallylphosphine, tetraallylsilane, 1,1,1-tris(hydroxymethyl)-propane-di- or triallyl ether, 2,2-bis(3-allyl-4-hydroxyphenyl)-propane, diallylcarbonate, and N,N'-diallyl-tartaric acid diamide.

6. The polymer according to claim 1, wherein the first monomer is a mixture comprising at least 50% by weight ethyl acrylate or wherein the first monomer is ethyl acrylate.

7. The polymer according to claim 6, wherein the first monomer is ethyl acrylate.

8. The polymer according to claim 6, wherein the first monomer is ethyl acrylate and wherein the crosslinking agent is pentaerythritol triallylether.

9. A hair styling composition comprising the polymer according to claim 1 in an amount of 0.1 to 5.0% by weight and comprising a thickener suitable for cosmetic compositions which is different from the polymer, in an amount of 0.1 to 3.0% by weight.

10. A hair styling composition comprising the polymer according to claim 1 in an amount of 0.1 to 10.0% by weight, wherein the hair styling composition does not comprise any thickener which is different from the polymer.

11. The hair styling composition according to claim 9, wherein the composition is a gel or a mousse or a pump spray or an emulsion.

12. The hair styling composition according to claim 11, wherein the composition is a transparent hair styling gel.

13. The polymer according to claim 1 for use in styling hair.

14. The polymer according to claim 1 wherein the crosslinking agent comprises pentaerythritol triallylether.

15. The hair styling composition according to claim 9 wherein the thickener comprises crosslinked polyacrylic acid.

\* \* \* \* \*